(12) United States Patent
Maschke

(10) Patent No.: US 8,792,964 B2
(45) Date of Patent: Jul. 29, 2014

(54) METHOD AND APPARATUS FOR CONDUCTING AN INTERVENTIONAL PROCEDURE INVOLVING HEART VALVES USING A ROBOT-BASED X-RAY DEVICE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1694 days.

(21) Appl. No.: 12/046,727

(22) Filed: Mar. 12, 2008

(65) Prior Publication Data

US 2009/0234444 A1 Sep. 17, 2009

(51) Int. Cl.
*A61B 5/05* (2006.01)

(52) U.S. Cl.
USPC ............... 600/427; 600/102; 600/424; 5/601; 5/600

(58) Field of Classification Search
USPC .......... 600/425, 407, 426; 378/197, 193, 196, 378/42, 189, 128, 98.12, 19, 114, 132; 414/146; 606/108; 5/600, 601
See application file for complete search history.

(56) References Cited

U.S. PATENT DOCUMENTS

| | | | |
|---|---|---|---|
| 4,819,751 A | 4/1989 | Shimada et al. | |
| 5,042,486 A | 8/1991 | Pfeiler et al. | |
| 5,345,940 A | 9/1994 | Seward et al. | |
| 6,059,731 A | 5/2000 | Seward et al. | |
| 6,298,261 B1 | 10/2001 | Rex | |
| 7,087,023 B2 | 8/2006 | Daft et al. | |
| 2001/0005410 A1* | 6/2001 | Rasche et al. ................. | 378/197 |
| 2002/0045817 A1* | 4/2002 | Ichihashi ...................... | 600/425 |
| 2005/0161051 A1* | 7/2005 | Pankratov et al. ............. | 128/898 |
| 2006/0074485 A1 | 4/2006 | Realyvasquez | |
| 2006/0120507 A1 | 6/2006 | Brunner et al. | |
| 2007/0016108 A1* | 1/2007 | Camus et al. ................. | 600/587 |
| 2007/0027390 A1* | 2/2007 | Maschke et al. .............. | 600/425 |
| 2007/0030945 A1 | 2/2007 | Boese et al. | |
| 2007/0173861 A1* | 7/2007 | Strommer et al. ............. | 606/108 |
| 2008/0218770 A1* | 9/2008 | Moll et al. .................... | 356/614 |
| 2008/0240363 A1 | 10/2008 | Grebner et al. | |
| 2008/0243064 A1* | 10/2008 | Stahler et al. ................ | 604/95.01 |

FOREIGN PATENT DOCUMENTS

WO WO 2004/103223 12/2004

OTHER PUBLICATIONS

"Percutaneous Valve Therapies: Where We Are and Where We Are Going," Feldman, Complex Coronary Intervention (2006).
"Percutaneous Valve Repair: Update on Mitral Regurgitation and Endovascular Approaches to the Mitral Valve," Dieter, Applications in Imaging—Cardiac Interventions (2003) pp. 11-14.
"Realization of Silicon Based Ultrasound Micro-Systems," Diss. ETH No. 13202—A Dissertation Submitted to the Swiss Federal Institute of Technology—Zurich—1999—Presented by Christoph Kuratli.

* cited by examiner

*Primary Examiner* — Long V. Le
*Assistant Examiner* — Lawrence Laryea
(74) *Attorney, Agent, or Firm* — Schiff Hardin LLP

(57) ABSTRACT

In a method and an apparatus for conducting minimally-invasive procedures involving heart valves at least one multi-access articulated x-ray imaging robot is employed that allows a radiation detector carried by the robot to be moved in arbitrary paths, such as in circle, an ellipse, or along a spiral, around a patient in order to generate multiple projection exposures of the relevant region of the patient during the procedure. An image processor reconstructs a 3D image from the projection exposures substantially in real time during the procedure, and the 3D image is displayed to operating personnel during the procedure.

19 Claims, 3 Drawing Sheets

METHOD AND APPARATUS FOR CONDUCTING AN INTERVENTIONAL PROCEDURE INVOLVING HEART VALVES USING A ROBOT-BASED X-RAY DEVICE

BACKGROUND OF THE INVENTION

1. Field of the Invention

The present invention concerns a method as well as an apparatus allowing an interventional procedure involving heart valves to be conducted using a robot-based x-ray device.

2. Description of the Prior Art

The reduction of the pumping power of one or both heart chambers is generally designated as a cardiac insufficiency. Cardiac insufficiency is not an actual illness, but rather is the result of various disease/pathology symptoms. As a result of cardiac insufficiency, the body and its organs do not receive the necessary amount of blood per unit of time. The vital organs are only insufficiently supplied with oxygen and nutrients.

Among the most important causes of cardiac insufficiency are illness of the coronary vessels (often after extended infarctions), hypertension that is insufficiently medically regulated, heart muscle illness, heart muscle infection (myocarditis), illness of the pericardium, and illness of the heart valves.

Congenital stenoses of one or more heart valves, or stenoses caused by other sources, such as, for example, calcium deposits, are frequent pathological conditions of the heart valves. Various types of interventional surgical procedures are known for addressing one or more of the above causes of cardiac insufficiency.

In the case of a pulmonary valve stenosis, the leaflets of the pulmonary valve are thickened, so that the opening of the valve is hindered. The right chamber therefore works against an increased resistance, and forms more muscle mass, i.e. it becomes hypertrophic.

In aortic valve stenosis, a narrowing or constriction of the discharge path of the left chamber occurs. The cause is a thickening of the valvular cusp and/or an underdevelopment of the aortic root. The constriction may be below the valve (sub-valvular), at the valve (valvular) or above the valve (supra-valvular). The left chamber works against an increased resistance and becomes thicker (becomes hypertrophic). Sub-valvular and supra-valvular aortic stenoses can generally be treated using balloon catheters.

Mitral stenosis is normally an acquired valve defect, and is almost always the result of rheumatic endocarditis.

Until the 1990's, heart valve stenoses normally were therapeutically treated by open heart procedures. Such procedures have high risks associated therewith as well as long recovery (convalescence) times for the patient.

The heart valves can be damaged by other illnesses, for example inflammation, influenza or cardiac infarction, to the extent that the valve must be replaced or surgically modeled.

Until recently, a replacement of a heart valve required an open heart procedure. Mechanical or biological heart valve prostheses were implanted (aortic valve, pulmonary valve) or the existing valve opening was surgically shaped (mitral valve and tricuspid valve). Such procedures also were associated with high risks and long recovery times (up to six weeks) for the patient.

More recently, methods have been developed to treat heart valve stenoses in a minimally-invasive manner by the use of specially designed catheters. In principle, all four heart valves are accessible for a balloon dilation (valvuloplasty), but dilation of the tricuspid valve is only rarely implemented, due to the relative rarity of tricuspid stenosis.

The basic steps of a number of known balloon dilation procedures are described below.

For balloon dilation in the case of pulmonary valve stenosis, after probing of the right or left pulmonary artery from the groin with an open-ended catheter, a relatively rigid guide wire is introduced. A special dilation catheter (valvuloplasty catheter) can be advanced via this guide wire after the catheter has been retracted.

This procedure is implemented under anesthesia, since filling of the balloon leads to a temporary interruption of circulation. In the case of less thickened valves, an excellent result with less residual resistance, and no or minimal insufficiency of the pulmonary valve, is achieved. In the case of a valve atresia, the targeted perforation of the valves by means of HF energy and subsequent balloon dilation is frequently possible.

Balloon dilation in the case of aortic valve stenosis resembles the procedure for balloon dilation in the case of pulmonary valve stenosis, in that a balloon catheter is advanced via a guide wire to the location of the valve. Generally, the probing is implemented in a retrograde manner, since the left ventricle is accessible via the stenotic aortic valve.

For balloon dilation in the case of mitral stenosis, the balloon catheter can be inserted into the mitral valve either in an antegrade manner from the left atrium (after transseptal puncture) or in a retrograde manner from the left ventricle. More recently, the antegrade procedure has prevailed. The size (area) of the opening (aperture) of the mitral valve can be doubled, for example, by means of balloon dilation.

A catheter suitable for this purpose is described in U.S. Pat. No. 4,819,751. Such catheters have the advantage of allowing a minimally-invasive cardiac procedure to be conducted therewith.

For approximately two years, methods in clinical testing allow a replacement or modeling of heart valves in a minimally-invasive manner by the use of special catheters.

Integration of an artificial heart valve into a stent that is placed in the aortic valve and the pulmonary valve with a catheter is described, for example, in the website www.corevalve.com. A detailed description can also be found in the article "Percutaneous Valve Therapies: Where We Are and Where We Are Going," by Feldman (www.tct.com).

A suitable heart valve for this purpose is described in United States Patent Application Publication No. 2006/0074485.

The shape of the mitral valve and/or the valve opening thereof can be modeled with catheter-based tools, for example with the commercially available Carillon Mitral Contour System, available from www.cardiacdimension.com. This catheter is conducted through the coronary sinus, and the procedure is known as percutaneous mitral annuloplasty.

A detailed description of known methods for repairing mitral valves can be found in the article "Percutaneous Valve Repair: Update on Mitral Regurgitation and Endovascular Approaches to the Mitral Valve," by Dieter.

A catheter device for insertion in an annuloplasty ring is described in PCT Application WO 2004/103233.

In contrast to the above-described diseases, diseases of the tricuspid valve are rare, but when found to exist, can be treated in procedures similar to those described above concerning the mitral valve.

A significant disadvantage of all of the recently developed minimally-invasive procedures is that they must be implemented using x-ray fluoroscopy, which shows only a 2D image of the heart and the catheter and tools located therein or proximate thereto. It is very difficult for a surgeon or cardiologist to mentally form spatial associations from such 2D images.

A further disadvantage associated with such known procedures is that when the catheter is clearly visible in such an x-ray image, the opening of the heart valve in question is only poorly visible, or vice versa. The opening can be shown more clearly by the injection of a contrast agent, but a significant number of patients are at risk of having an allergic reaction to conventional contrast agents.

Due to these limitations in the content of the displayed images, a risk exists that the stenosis will not be correctly opened, or an artificial (replacement) heart valve may not be correctly placed.

It is also known to conduct some of these procedures, or portions thereof, supported by extracorporeal or intracorporeal (ICE, TEE) ultrasound imaging, but generally this does not provide a sufficient image quality.

In theory, imaging in the context of the aforementioned known procedures could be improved by the use of a C-arm x-ray device, such as the CardDynaCT available from Siemens Medical Solutions. With this device, 2D soft tissue exposures as well as 3D high contrast exposures (with the injection of contrast agent) of a beating heart can be produced.

In practice, however, the aforementioned commercially available C-arm x-ray device, as well as other commercially available C-arm x-ray devices, does not provide adequate access to the patient in order to permit percutaneous heart valve procedures to be implemented by operating personnel.

SUMMARY OF THE INVENTION

An object of the present invention is to provide a method and an apparatus that allows minimally-invasive interventional procedures of the type described above to be conducted with improved imaging support.

The above object is achieved in accordance with the present invention by a method and an apparatus for conducting minimally-invasive procedures involving heart valves wherein at least one multi-axis articulated x-ray imaging robot is employed that allows a radiation detector carried by the robot to be moved in arbitrary paths, such as in circle, an ellipse, or along a spiral, around a patient in order to generate multiple projection exposures of the relevant region of the patient.

The articulated robot has four degrees of freedom, and preferably has six degrees of freedom.

3D images, including 3D soft tissue images, can be reconstructed from the projection exposures obtained with the articulated robot x-ray imaging system.

A multi-axis articulated robot suitable for use in the inventive method and apparatus is described in DE 10 2005 012 700 A1, the teachings of which are incorporated herein by reference. In that document, however, there is no mention or discussion of the use of such a robot imaging system for procedures involving heart valves.

Moreover, a procedure is described in United States Patent Application Publication No. 2007/0030945 wherein a 3D representation of the relevant anatomy of a heart, in particular soft tissue images, ensues with the use of ECG gating. The procedure described therein can operate with or without x-ray contrast agent for presentation of the relevant anatomy. Combined forms are also possible, meaning that exposures can be made with and without contrast agent and can be superimposed with each other or subtracted from one another. The teachings of United States Patent Application Publication No. 2007/00030945 are incorporated herein by reference.

The respective points in time at which the projection exposures are generated can be registered, so that a 4D presentation can be reconstructed therefrom.

The robotic imaging device has at least one x-ray source and at least one x-ray detector. By manipulation of the robot arm the x-ray source can be positioned over or under the patient support (patient bed). It is also possible for the x-ray source to be mounted on a first robot and the x-ray detector to be mounted on a second robot. The robot arm or arms can be arranged on mobile carriers that allow flexible positioning in space by means of rollers, wheels, chain drive, etc. The movement in space of robot arm or arms can be accomplished by motorized actuators.

The x-ray source and the detector can be mounted at the robot arm by a C-arm, a U-frame, or some other type of common holder. The base of the robot can be permanently mounted in the operating facility, such as on the ceiling, wall or floor of the operating room.

The patient support has an x-ray-transparent support surface, as is common. The supporting surface of the patient support can be spatially shifted manually, or in a motorized manner, in terms of height, longitudinal direction and transverse direction. The patient support can be floor-mounted, or can be supported by a further robot arm. The patient support can be tilted as needed in any of the x, y or z directions of a Cartesian coordinate system. The patient support can be rotatable around an isocenter. The patient support may additionally be able to execute circular or elliptical rotational movements around a fixed point in a plane, or a fixed point in space.

The basic components of the overall device are at least one x-ray tube with a radiation diaphragm, a patient table, a digital imaging system for fluoroscopic exposures, and system controller, a voltage generator, a radiation detector, as well as operating and display units. The x-ray detector is preferably an aSi detector.

The operating units preferably allow standardized selection possibilities, know as organ programs or examination programs. If an examination program (for example, aortic valve replacement) is selected, all system components, the image processing, the x-ray source, the radiation detector, and the table positions are set by the system controller, and are automatically assumed.

A collision-avoidance unit or system can be provided that monitors critical positions of the movable components, and generates an alarm if and when a collision between components, or with operating personnel, is imminent, and may also prevent further movement after a limit range has been reached.

A patient proximate operating unit can be provided that allows manual operation, supported by motors, of the robot arm by an operator. For this purpose, measurement sensors are connected into the robot arm that activate the motorized components or increase the motorized force, after exceeding a defined limit.

A small, articulated robot can be provided to take over or support the control guidance of the heart valve catheter. This small robot can be mounted in proximity to the patient.

An ultrasound device can additionally be integrated into the system, to which an extracorporeal transducer and an intracorporeal transducer can be connected for operation in a known manner.

The x-ray exposures can be superimposed with the ultrasound exposures by an image fusion unit.

Interfaces and image processing units can be provided to integrate further endoscopic or catheter-based image processing devices, such as any of OCT, IVUS, IVMRI, ICE or TEE, as well as to superimpose such images with the x-ray images.

A device for spatial tracking of the catheter and instruments can be provided, such a tracking device operating with electromagnetic position sensors, as described in U.S. Pat. No. 5,042,486, or operating using ultrasound, as described in DE 198 52 467 A1.

Additionally, an ablation device can be integrated into the system to implement ablation procedures at the heart valve, for example, HF procedures or cryo procedures.

A heart pacemaker unit can be provided to temporarily artificially beat the heart as needed. An anesthesia ventilator can also be provided in the system.

DESCRIPTION OF THE PREFERRED EMBODIMENTS

Figure 1:
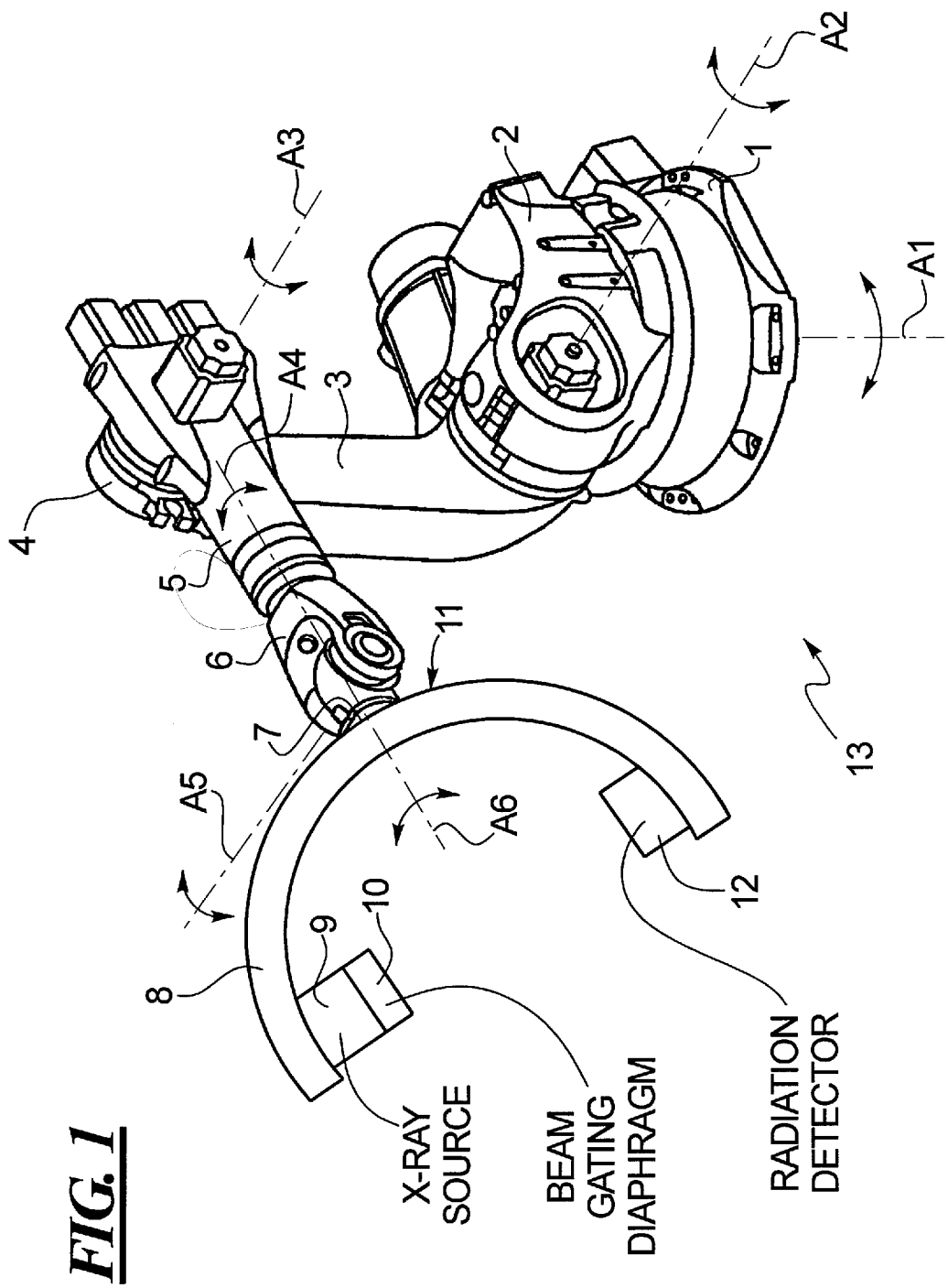
FIG. 1 in perspective view, shows a robot arm x-ray image acquisition system suitable for use in accordance with the inventive method system.

A robot arm x-ray image acquisition system 13 is shown in FIG. 1 of the type described in DE 10 2005 012 700 A1, for purposes other than implementing minimally invasive procedures involving heart valves. The robotic portion of the device 13 is mounted to a base 1 which, in this embodiment, is shown as a base affixable to the floor of a room in which the device 13 is used. The device 13, however, may also be wall-mounted or sealing-mounted. A shoulder articulation 2 is rotatably mounted on the base 1, so as to be rotatable around a substantially vertical axis A1. The shoulder articulation is connected to a first arm portion 3 of an arm articulation, so that the first arm portion 3 is rotatable around a substantially horizontal axis A2. The first arm portion 3 is connected via an elbow articulation 4 to a second arm portion 5. The first arm portion 3 and the second arm portion 5 are rotatable relative to each other around a substantially horizontal axis A3 of the elbow articulation 4.

The second arm portion 5 carries a wrist articulation 6, which is rotatable relative to the second arm portion 5 around an axis A4. The wrist articulation 6 also includes a further articulation joint connected to a mount 7 for, in this embodiment, a C-arm 11. The holder 7 and the C-arm 11 connected thereto are rotatable around an articulation axis A5 in the wrist articulation 6, and the holder 7 and the C-arm 11 are also rotatable around a further articulation axis A6. The C-arm 11 includes a curved support 8, to which an x-ray source 9 and a radiation detector 12 are mounted for co-rotation with the support arm 8. A beam gating diaphragm 10 is disposed in front of the x-ray source 9, so as to be in the path of an x-ray beam that is emitted from the x-ray source 10 that propagates to the radiation detector 12. Alternatively, a beam gating diaphragm could be placed in proximity to the radiation detector 12.

Figure 2:
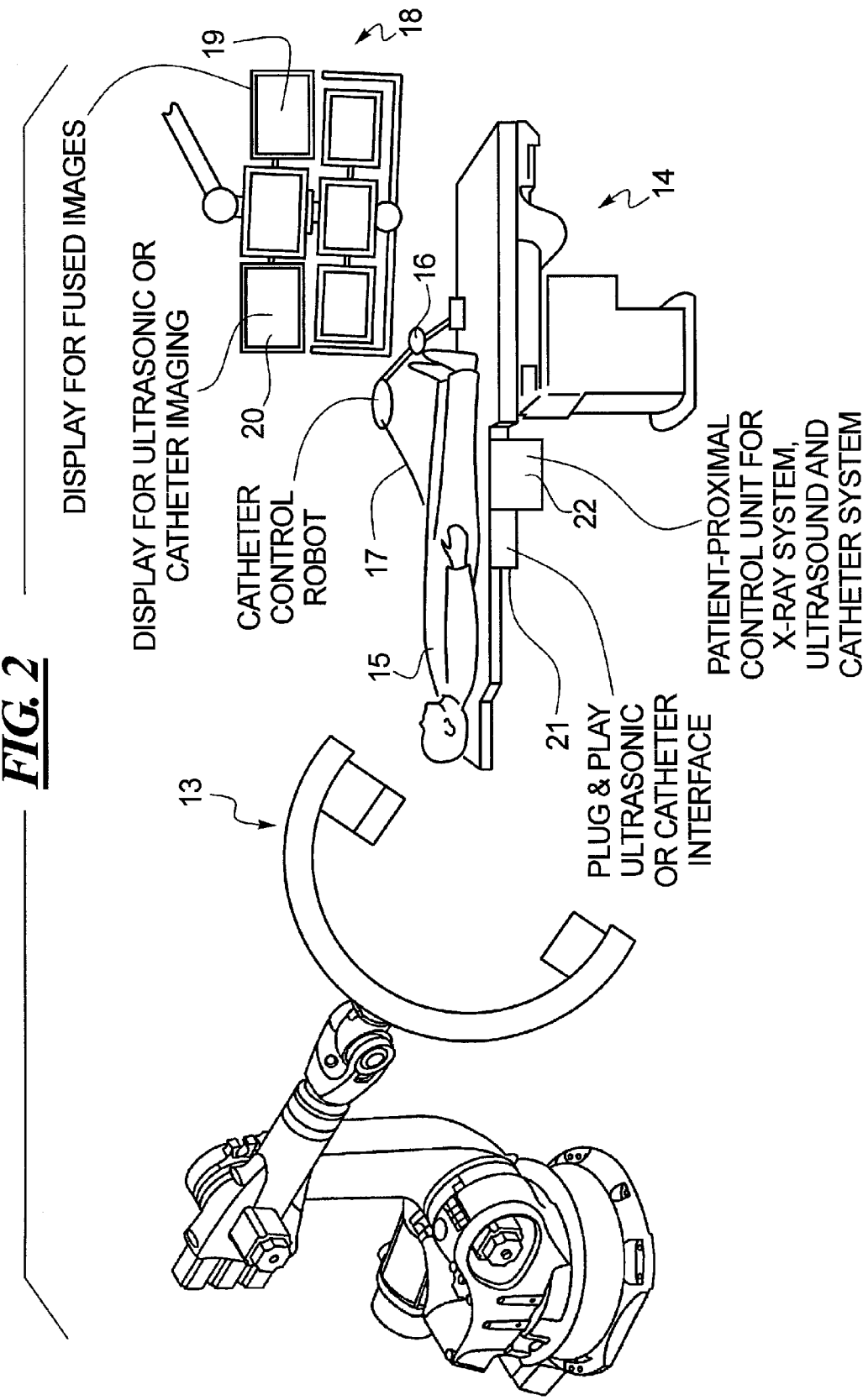
FIG. 2 illustrates the basic structural components of a system constructed and operating in accordance with the present invention.

As shown in FIG. 2, the robotic imaging device 13 is usable in combination with a table support 14 for a patient 15. Because of the numerous degrees of freedom provided by the robotic arm imaging device 13, and the non-restrictive access that is associated therewith, the system shown in FIG. 2 is suitable for implementing the various types of minimally-invasive procedures involving heart valves that were initially described. Many of these procedures require implementation of a catheter 17, which in the inventive system can be automatically or semi-automatically operated by a catheter control robot 16. A bank 18 of monitors or displays is provided that includes displays for separately displaying conventional types of images that are used in the aforementioned procedures. In accordance with the invention, however, these displays include a display for fused images 19 and a display for ultrasonic or catheter imaging 20. One or more of the displays in the bank 18 can display a three-dimensional image that is generated from multiple projections of the region of interest of the patient 15 acquired by the robotic image acquisition system 13.

The system can be provided with a plug & play ultrasonic or catheter interface 21, if an ultrasound catheter is used. The system can also be provided with a patient-proximal control unit 22, for operating the x-ray system, the ultrasound system and the catheter system from a single location.

Figure 3:
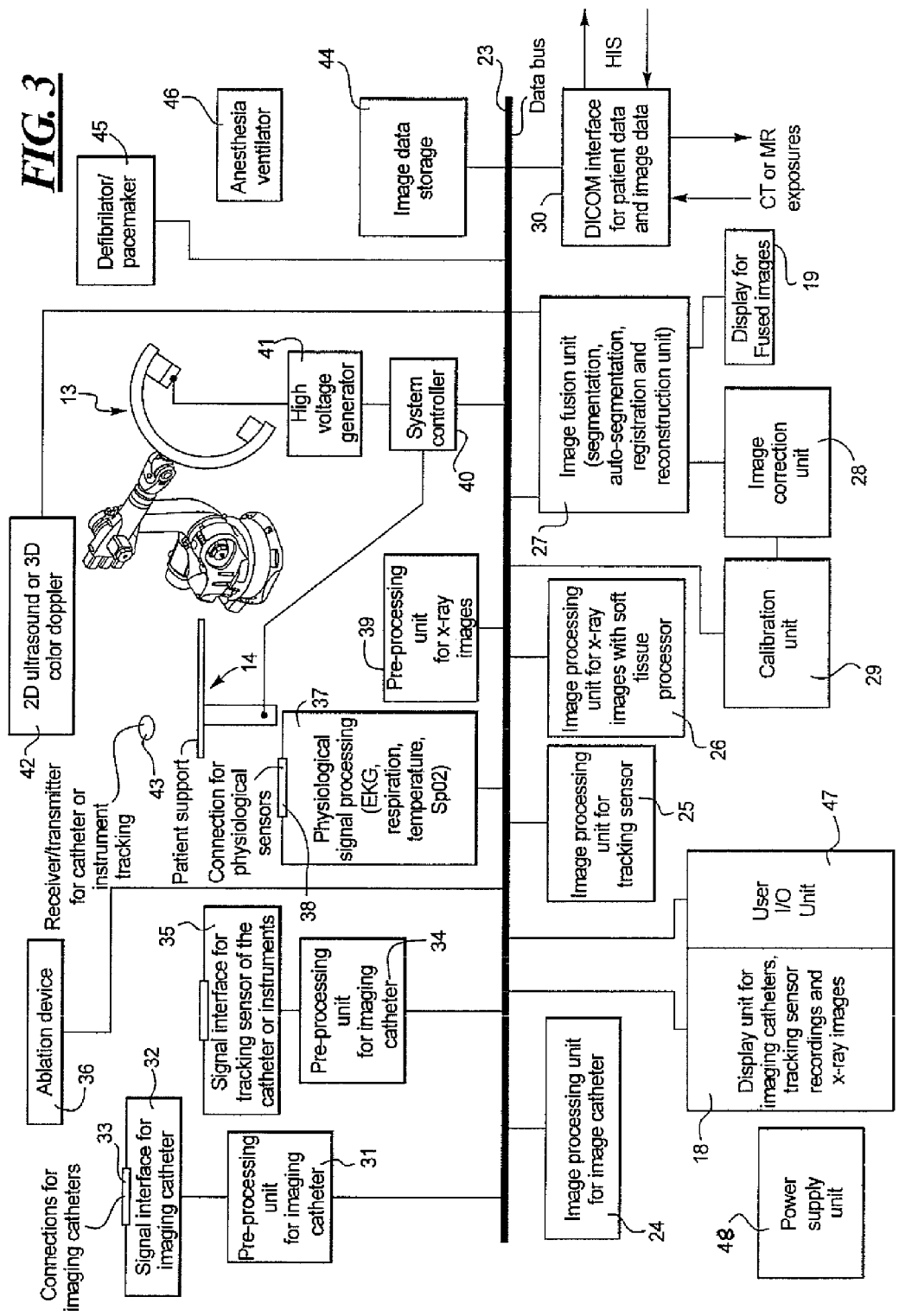
FIG. 3 is a detailed block diagram of an exemplary embodiment of the system of FIG. 2.

A more detailed block diagram presentation of the system of FIG. 2 is shown in FIG. 3. All components are connected to a data bus 23, which serves for transferring data as well as control instructions, as needed, between and among the various components.

These components include an image processing unit 24 for processing images obtained with an imaging catheter, such as an IVUS catheter or an optical catheter. Connected to the data bus 23 is also an image processing unit 25 for a tracking sensor that is associated with the image catheter, or another interventional instrument. Also connected to the data bus 23 is an image processing unit 26 for x-ray images, which includes a soft tissue processor, for generating images wherein soft tissue is accurately displayed.

Also connected to the data bus 23 is an image fusion unit 27 connected to the aforementioned display for fused images 19.

The data bus 23 is also in communication with a DICOM interface 30 for patient data, such as obtained from and transmitted to a hospital information system HIS, and for receiving and transmitting images such as CT exposures and/or MR exposures.

The image fusion 27 is capable of performing functions such as image segmentation, auto-segmentation, image registration and image reconstruction based on data supplied thereto, such as from the robotic imaging device 13 or from archived images received via the DICOM interface 30. The image fusion unit is connected to an image correction unit 28 which is, in turn connected to a calibration unit 29, the latter also being in direct communication with the data bus 23.

An image data storage 44 is also connected to the data bus 23, for storing any images generated during the minimally-invasive procedure involving heart valves, and for supplying images for display during that procedure, that have been previously obtained and stored.

Each of the image processing units 24, 25, 26, and the image fusion unit 27, and the image data storage 44 communicate with the display bank 18 (shown in FIG. 2) via the data bus 30. A user I/o unit 47 is also in communication with other components via the data bus 30.

All units requiring power for operation thereof are supplied by a power supply unit 48.

Other components that will be most likely physically present in the operating room are shown above the data bus 23 in FIG. 3. In addition to the already-described robotic imaging device 13, these include a high-voltage generator 41 that supplies the necessary voltages and currents to the x-ray source 9, under the control of a system controller 40, which also operates the patient table 14.

A preprocessing unit 39 for processing the x-ray image data obtained from the radiation detector 12. For this purpose, the preprocessing unit 39 is in direct or wireless communication with the radiation detector 12.

A physiological signal processor 37 is provided for monitoring functions such as ECG, respiration, body temperature, blood oxygen concentration, etc. This processor 37 has an interface 38 for connection to appropriate physiological sensors.

A preprocessing unit 34 for processing image data from the imaging catheter is also connected to the data bus 23, which has a signal interface 35 for the tracking sensor of the catheter or other instruments.

Since more than one imaging catheter may be employed or more than one type of imaging catheter may be employed, FIG. 3 also shows a further preprocessing unit 31 for the imaging catheter, having a signal interface 32, and connections 33 to the imaging catheter.

If desired, the system may also be provided with an ablation device 36, which is connected to the data bus 23 so that it can be operated by the system controller 40. The same is true with regard to a defibrillator/pacemaker 45.

An extracorporeal ultrasound system 42 may also be provided, in the form of a 2D ultrasound system or a 3D color Doppler system, also connected to the data bus 23 so that it can be communicate with the image fusion unit 27.

For the aforementioned tracking of the catheter, catheters, or other instruments, a receiver/transmitter 43 is provided that can operate electromagnetically or according to any other known tracking mode.

An anesthesia ventilator 46 can also be provided with appropriate user interfaces and interfaces to the patient. Since such a unit is typically a stand-alone unit operated by an anesthesiologist, it is not shown as being connected to the data bus 23, although such a connection is possible, if desired.

Although modifications and changes may be suggested by those skilled in the art, it is the intention of the inventor to embody within the patent warranted hereon all changes and modifications as reasonably and properly come within the scope of his contribution to the art.

I claim as my invention:

1. A system for conducting medical interventional procedures involving heart valves, comprising:
    a patient table configured to support a patient thereon;
    a catheter system configured to interact with the patient on the patient table to implement a medical procedure involving a heart valve of the patient, said catheter system comprising a catheter and a catheter robot that at least semi-automatically manipulates said catheter intracorporeally in the patient;
    a robotic x-ray imaging device comprising a robot arm having at least four degrees of freedom and a support arm carried by said robot arm, to which are mounted an x-ray source that emits x-rays and a radiation detector, said robot arm being operable to irradiate a region of the patient comprising said heart valve with said x-rays during said medical procedure from a plurality of different projection directions, with said radiation detector detecting x-rays attenuated by the patient at said different projection directions and emitting respective sets of projection data for said projection directions;
    a control unit in communication with said catheter robot and said robotic x-ray imaging device, said control unit being mounted at said patient table and being configured to operate both said catheter system, including said catheter robot thereof, and said robotic x-ray imaging system from a single location at said patient table;
    an image processor in communication with said radiation detector and supplied therefrom with the projection data sets that reconstructs a 3D image of said region from said projection data sets substantially in real time during said medical procedure; and
    a display in communication with said image processor on which said 3D image is displayed during said medical procedure.

2. A system as claimed in claim 1 wherein said robot arm has six degrees of freedom.

3. A system as claimed in claim 1 wherein said support comprises a C-arm.

4. A system as claimed in claim 1 comprising a further imaging device that obtains a further image, different from said 3D image, of said heart valve.

5. A system as claimed in claim 4 wherein said further imaging device is an intracorporeal imaging device embodied in said catheter.

6. A system as claimed in claim 5 wherein said intracorporeal imaging device is selected from the group consisting of intracorporeal optical imaging devices, intracorporeal magnetic resonance imaging devices, and intracorporeal ultrasound imaging devices.

7. A system as claimed in claim 4 comprising an image fusion unit that generates a fused image comprising of said 3D image and said further image.

8. A system as claimed in claim 7 wherein said image fusion unit comprises a segmentation unit that implements a segmentation of said 3D image prior to fusion with said further image.

9. A system as claimed in claim 5 wherein said control unit is configured to also operate said intracorporeal imaging device from said single location.

10. A system as claimed in claim 1 comprising a tracking system that tracks intracorporeal movement of said catheter in the patient.

11. A system as claimed in claim 1 wherein said catheter system is configured to implement a balloon dilation procedure for treatment of stenosis of said heart valve.

12. A method for conducting a medical interventional procedure involving heart valves, comprising the steps of:
    placing a patient on a patient table;
    implementing a medical procedure involving a heart valve using a catheter system, comprising catheter and a catheter robot, by robotically manipulating said catheter intracorporeally in said patient with said catheter robot;
    from a single control unit at said patient table, controlling both said catheter system, including said catheter robot thereof, and said robot arm from a single location at said patient table;
    during said medical procedure, obtaining a plurality of projection data sets of a region of the patient comprising said heart valve by moving an x-ray source and a radiation detector around the patient with a robot arm having at least four degrees of freedom to obtain said projection data sets respectively at a plurality of projection directions;
    reconstructing a 3D image from said plurality of projection data sets substantially in real time during said medical procedure; and
    displaying said 3D image during said medical procedure.

13. A method as claimed in claim 12 wherein the step of implementing a medical procedure involving a heart valve comprises implementing a balloon dilation procedure to treat stenosis of said heart valve.

14. A method as claimed in claim 12 comprising obtaining a further image of said region, different from said 3D image, during said medical procedure.

15. A method as claimed in claim 14 comprising fusing said 3D image and said further image to produce a fused image, and displaying said fused image during said medical procedure.

16. A method as claimed in claim 15 comprising segmenting said 3D image to obtain a segmented image, and fusing said segmented image with said further image.

17. A method as claimed in claim 14 comprising embodying an imaging device in said catheter and intracorporeally obtaining said further image with said imaging device.

18. A method as claimed in claim 17 comprising intracorporeally obtaining said image using an imaging modality selected from the group consisting of intracorporeal optical imaging, intracorporeal magnetic resonance imaging, and intracorporeal ultrasound imaging.

19. A method as claimed in claim 17 comprising also operating said imaging device from said control unit at said single location to intracorporeally obtain said further image.

\* \* \* \* \*